United States Patent [19]
Landau et al.

[11] Patent Number: 6,132,395
[45] Date of Patent: Oct. 17, 2000

[54] NEEDLELESS SYRINGE WITH PREFILLED CARTRIDGE

[75] Inventors: Sergio Landau, Laguna Niguel, Calif.; James M. Bonicatto, Portland, Oreg.

[73] Assignee: Bioject, Inc., Portland, Oreg.

[21] Appl. No.: 09/207,398

[22] Filed: Dec. 8, 1998

[51] Int. Cl.$^7$ ...................................................... A61M 5/30
[52] U.S. Cl. ........................... 604/68; 604/236; 604/238; 604/249
[58] Field of Search ...................................... 604/118, 131, 604/121, 140, 141, 146, 156, 218, 231, 232, 236, 238, 249, 264, 68

[56] References Cited

U.S. PATENT DOCUMENTS

| | | |
|---|---|---|
| 3,729,031 | 4/1973 | Baldwin . |
| 3,940,003 | 2/1976 | Larson . |
| 3,941,128 | 3/1976 | Baldwin . |
| 4,592,745 | 6/1986 | Rex et al. . |
| 4,662,878 | 5/1987 | Lindmayer . |
| 4,713,061 | 12/1987 | Tarello et al. . |
| 4,747,839 | 5/1988 | Tarello et al. . |
| 4,790,824 | 12/1988 | Morrow et al. . |
| 4,850,967 | 7/1989 | Cosmai . |
| 4,886,495 | 12/1989 | Reynolds . |
| 4,909,794 | 3/1990 | Haber et al. . |
| 4,940,460 | 7/1990 | Casey et al. . |
| 4,941,880 | 7/1990 | Burns . |
| 5,024,656 | 6/1991 | Gasaway et al. ........................ 604/70 |
| 5,135,514 | 8/1992 | Kimber . |
| 5,273,544 | 12/1993 | Van der Wal . |
| 5,364,386 | 11/1994 | Fukuoka et al. . |
| 5,399,163 | 3/1995 | Peterson et al. . |
| 5,462,535 | 10/1995 | Bonnichsen et al. . |
| 5,472,022 | 12/1995 | Michel et al. . |
| 5,573,513 | 11/1996 | Wozencroft . |
| 5,716,348 | 2/1998 | Marinacci et al. . |

FOREIGN PATENT DOCUMENTS

97/00812  3/1997  WIPO .

*Primary Examiner*—Sharon Kennedy
*Assistant Examiner*—Eric Kline
*Attorney, Agent, or Firm*—Kolisch, Hartwell, Dickinson, McCormick & Heuser

[57] ABSTRACT

A cartridge and nozzle assembly for use in a needless injection system is provided. The assembly includes: (1) a cartridge having a plunger disposed at a rearward end thereof, and including a throat at a forward portion thereof, with a displaceable outlet valve initially disposed within the throat, the outlet valve being formed of resilient material and having at least one axial channel defined in the forward and rearward portions thereof, between which is disposed a channel-less valve body; (2) a nozzle for receiving the cartridge, the nozzle defining a rearward, cartridge-receiving portion, and including a forward portion terminating in and defining a valve abutment surface with an injection orifice defined therein and a recessed portion, the recessed portion being configured to receive the valve when the valve is displaced to a forwardly disposed position such that the valve is disposed against the valve abutment surface, and so that the inner portion of the cartridge has fluid access to the orifice via the axial channels and around the valve body; and (3) a seal disposed between the cartridge and the nozzle adjacent the forward portions thereof for at least reducing leakage of injectate therebetween.

17 Claims, 8 Drawing Sheets

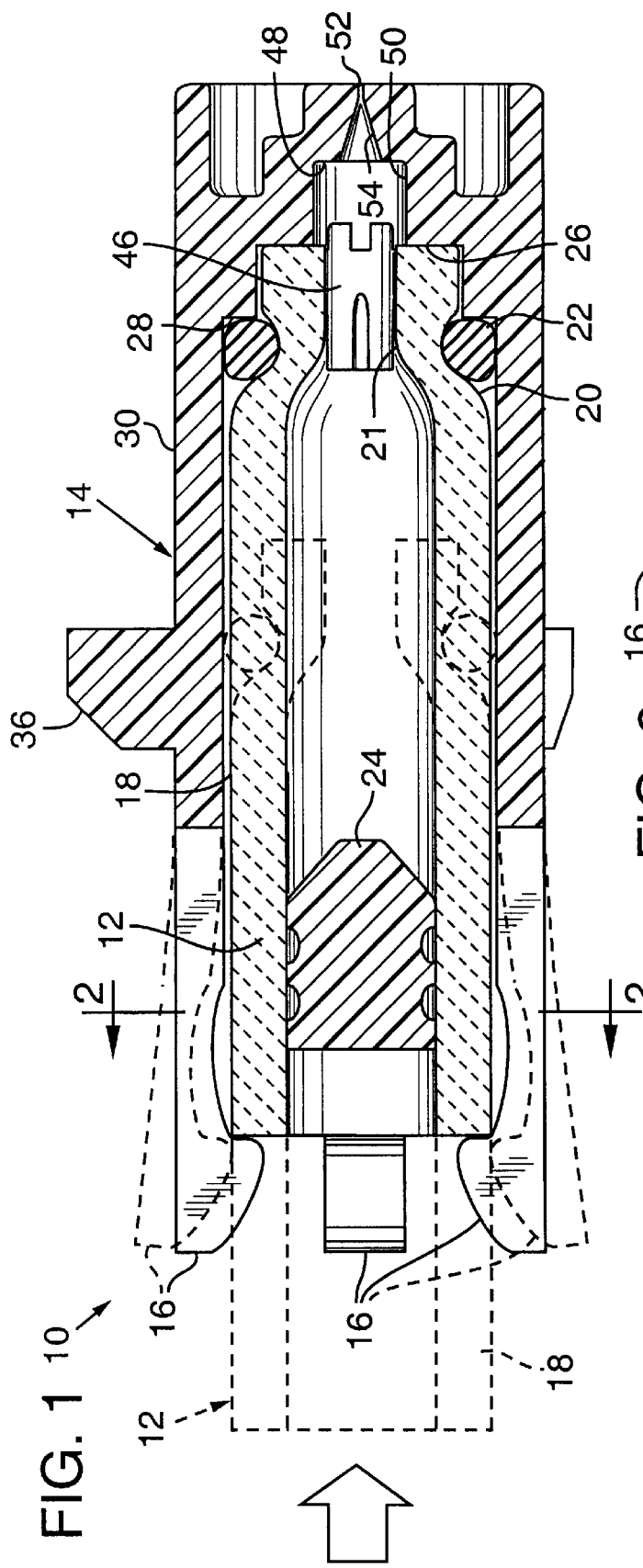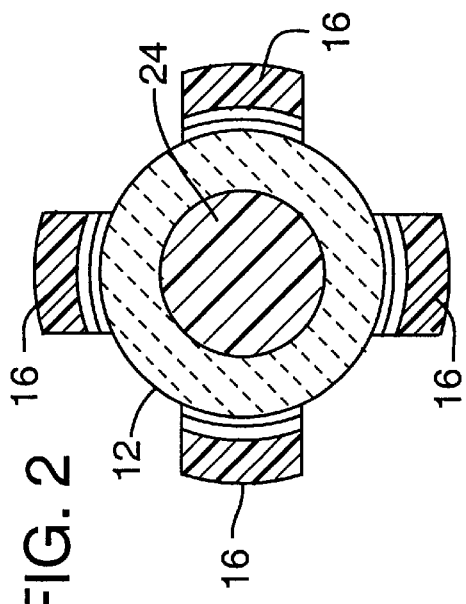

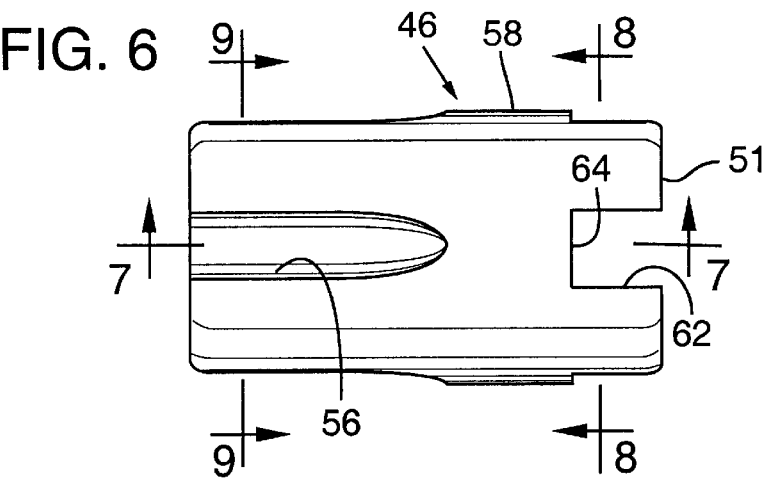
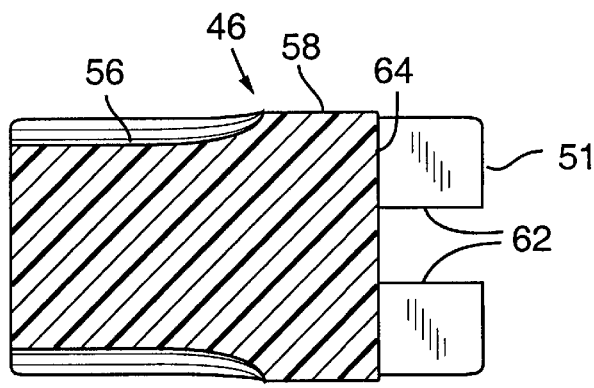
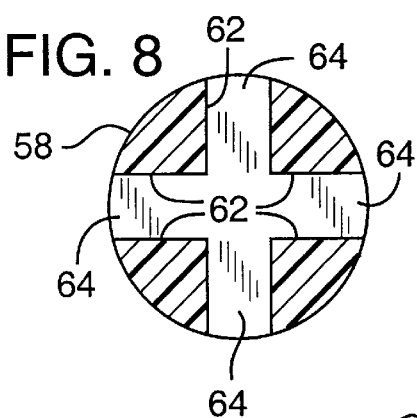
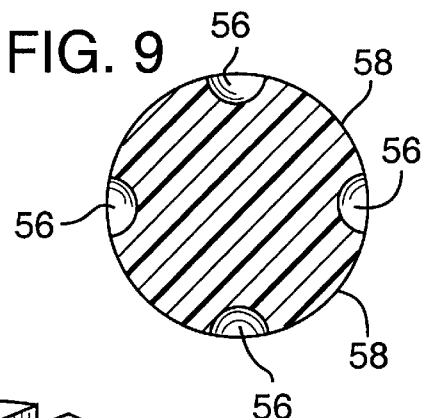
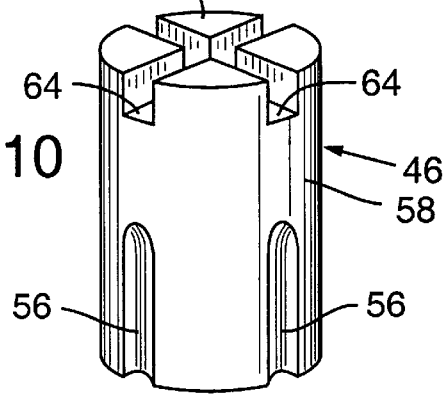

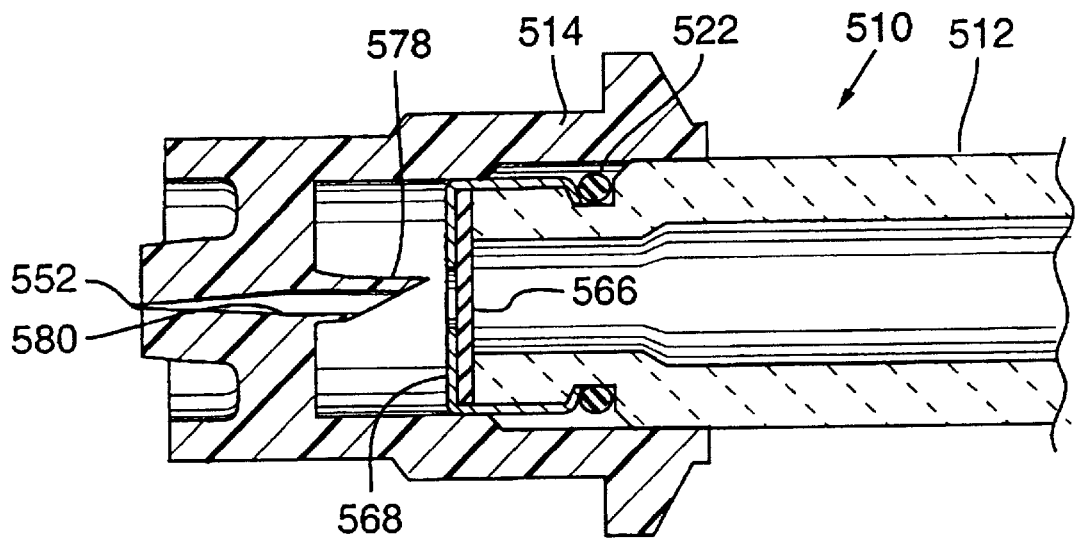
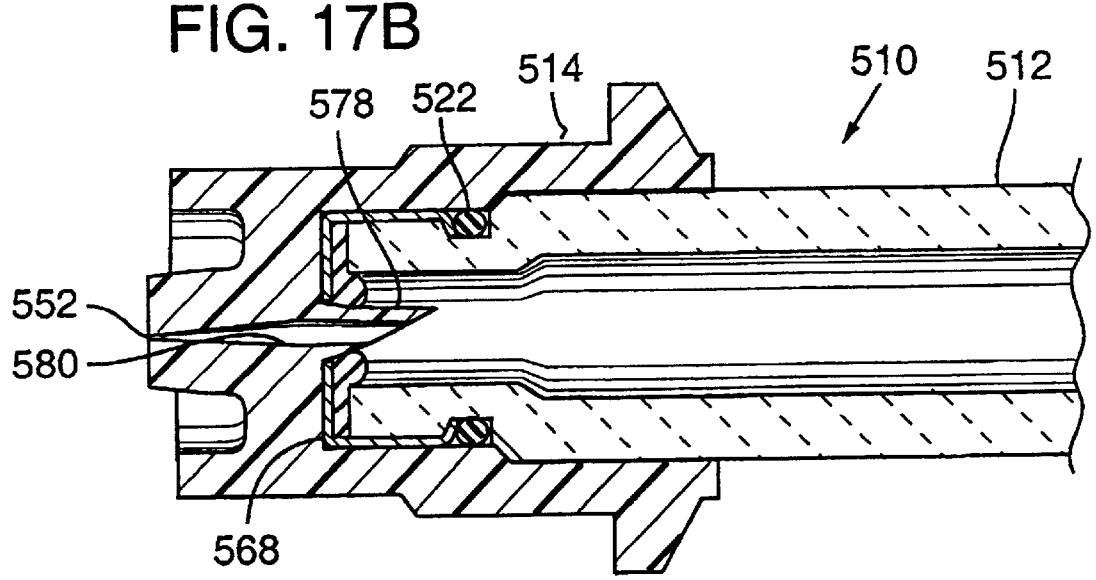

NEEDLELESS SYRINGE WITH PREFILLED CARTRIDGE

BACKGROUND OF THE INVENTION

This invention relates to a needleless injection system which includes a prefilled cartridge.

One of the problems inherently present in the packaging of liquid parenteral drugs is that there is not enough biocompatibility data about the interaction between those drugs and thermoplastic containers. While plastic is commonly used in many injection devices, most parenteral drugs cannot be exposed to most plastics other than for a short period immediately prior to the injection. This is because the drug or injectate may chemically react with the plastic, or cause materials in the plastic to leach into the injectate, thereby introducing impurities in the drug. In periods of extended storage, such exposure to a plastic container may result in degradation of the drug. For these reasons, the pharmaceutical industry normally avoids the storage of injectate in some thermoplastic materials such as polypropylene, which is commonly used in syringes and related injection paraphernalia. Similarly, there is no long term biocompatibility data on engineering or high strength thermoplastics, such as polycarbonate, which is the plastic most commonly used in needleless injection systems.

For this reason, injectates are typically stored in glass vials. Immediately prior to injection, the injectate chamber of a needleless injection system is filled from a glass vial containing the drug. This normally requires the use of a vial adapter, sometimes referred to as a blunt fill device, or an access needle which pierces the protective membrane over the top of the vial and then directs injectate down into the chamber or cartridge of the needleless injection system.

There are a number of drawbacks with this conventional approach. For example, the extra step of having to transfer the drug from the glass vial to the needleless injection system is time consuming and can be troublesome to a patient who is trying to administer the drug at home and who may have physical infirmities. Even for those who are not infirm, an adapter must be on-hand, and it must be sterile to prevent contamination of the injectate. The adapter typically includes a transfer needle with a sharp point at one end to pierce the vial membrane, and that can lead to injury, to unintended introduction of the injectate into the handling personnel or administrator, and/or to contamination of the injectate. This extra step of filling the needleless injection system immediately prior to injection also brings about the possibility of leakage and waste of injectate and, if improperly performed, can introduce air into the injection system. The introduction of air presents difficulties in a needleless injection system, because unlike a conventional needle and syringe system, it is not easy to bleed air out of the chamber of a needleless device. Therefore, firing the injection system with a portion of its chamber filled with air results in a lower dosage being injected into the patient. It is also possible that the injection may take place at an improper pressure. One advantage of the needleless injection systems of Bioject, Inc., assignee of this patent, is that they are able to inject a precisely predetermined amount of injectate at a predetermined, precise location in the tissue of the patient. The introduction of air may make it difficult to achieve such precision.

Accordingly, it is an object of the present invention to provide for the prefilling of a cartridge to be used in a needleless injection system.

SUMMARY OF THE INVENTION

A cartridge and nozzle assembly for use in a needless injection system is provided. The assembly includes: (1) a cartridge having a plunger disposed at a rearward end thereof, and including a throat at a forward portion thereof, with a displaceable outlet valve initially disposed within the throat, the outlet valve being formed of resilient material and having at least one axial channel defined in the forward and rearward portions thereof, between which is disposed a channel-less valve body; (2) a nozzle for receiving the cartridge, the nozzle defining a rearward, cartridge-receiving portion, and including a forward portion terminating in and defining a valve abutment surface with an injection orifice defined therein and a recessed portion, the recessed portion being configured to receive the valve when the valve is displaced to a forwardly disposed position such that the valve is disposed against the valve abutment surface, and so that the inner portion of the cartridge has fluid access to the orifice via the axial channels and around the valve body; and (3) a seal disposed between the cartridge and the nozzle adjacent the forward portions thereof for at least reducing leakage of injectate therebetween.

Another aspect of the invention provides a cartridge and nozzle assembly for use in a needleless injection system, comprised of the following components: (1) a cartridge having a plunger disposed at a rearward end thereof, and including a throat at a forward portion thereof; (2) a membrane disposed across the cartridge throat which breaks when a predetermined amount of pressure is applied to fluid in the cartridge; and (3) a nozzle for receiving the cartridge, the nozzle defining a rearward, cartridge receiving portion, and including a forward portion termination in and defining an injection orifice, with the inner portion of the cartridge having fluid access to the orifice when the membrane is broken.

Yet another aspect of the invention is a method of providing a needleless injection for a patient. The method includes the following steps, not necessarily in the recited order: (1) selecting a resilient valve having a plurality of channels defined therein and a body portion disposed between the channels; (2) selecting a cartridge having a forward throat conforming to the body of the valve; (3) placing the valve within the cartridge throat; (4) filling the cartridge with liquid injectate; (5) installing a plunger in the rear end of the cartridge; (6) selecting a nozzle with a rearward cartridge-receiving portion and a forward portion defining a recess for non-sealably receiving the valve and an aperture for facilitating injection of injectate therethrough; (7) installing the cartridge into the nozzle to form a cartridge/nozzle assembly; and (8) mounting the cartridge/nozzle assembly into a needleless injection system by pushing the plunger rearwardly against a ram to forwardly displace the plunger, causing pressure of injectate within the cartridge to forwardly displace the valve into the nozzle recess to permit injectate to flow around the body, through the channels, and into the aperture.

BRIEF DESCRIPTION OF THE DRAWINGS

FIG. 1 is a side elevation sectional view of the prefilled cartridge of the present invention, with its initial position prior to insertion of the cartridge shown in phantom, and the inserted position, prior to initial pressurization, shown in solid lines;

FIG. 2 is an end elevation sectional view taken along line 2—2 of FIG. 1, showing the cartridge in its inserted position;

FIG. 6 is an enlarged side elevation view of the outlet valve of the embodiment of FIG. 1;

FIG. 7 is a side elevation sectional view taken along line 7—7 of FIG. 6;

FIG. 8 is an end elevation sectional view taken along line 8—8 of FIG. 6 showing the forward portion of the outlet valve;

FIG. 9 is an end elevation sectional view taken along line 9—9 of FIG. 4 showing the rearward portion of the outlet valve;

FIG. 10 is an isometric view of the outlet valve of FIGS. 1–9.

FIG. 17A is a side elevation sectional view of another alternate embodiment, with the cartridge in a partially inserted position in the nozzle; and FIG. 17B is a side elevation sectional view of the embodiment of FIG. 17A except that the cartridge is shown in its fully-inserted position.

DETAILED DESCRIPTION OF THE PREFERRED EMBODIMENTS

The Embodiment of FIGS. 1–10

Figure 3:
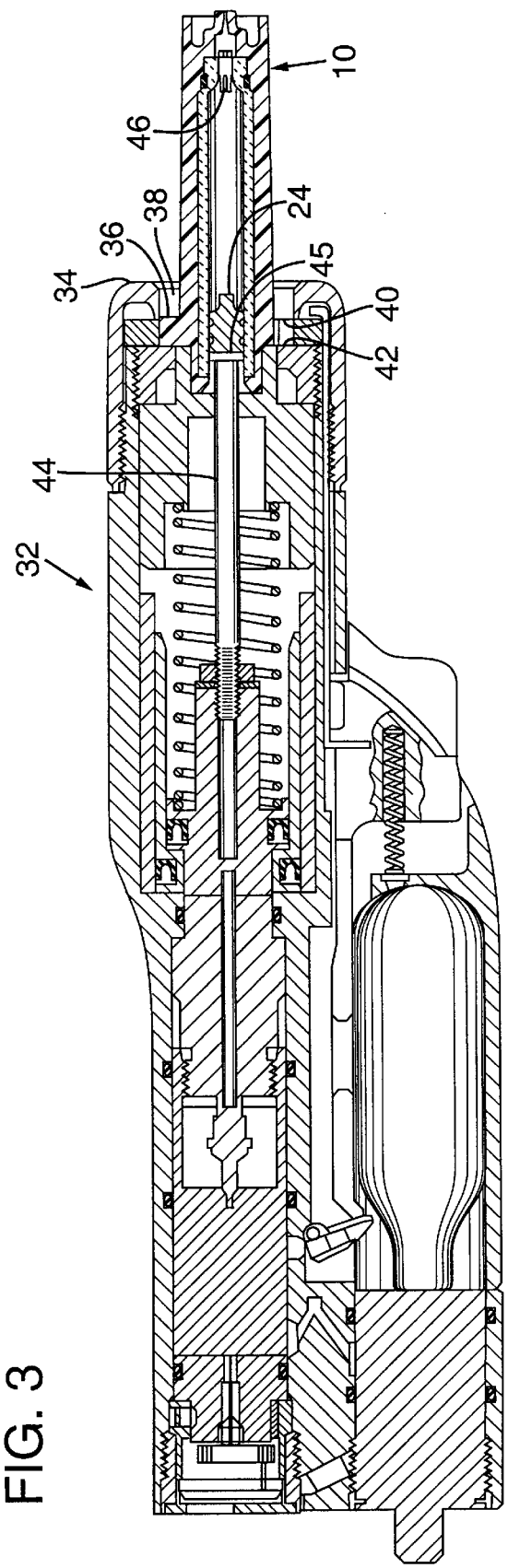
FIG. 3 is a side elevation sectional view showing the position of the cartridge and nozzle within a preferred embodiment of the needleless injection system.

One form which the invention may take is depicted in FIGS. 1–10. This description will initially make reference to those figures. Depicted generally at 10 is a cartridge/nozzle assembly in which the cartridge may be prefilled with liquid injectate. The assembly includes a cartridge 12 which, in the preferred embodiment, is formed of strengthened glass, and a nozzle 14, which, in the preferred embodiment, is fabricated of high strength thermoplastic, typically polycarbonate. The nozzle 14 is of conventional design except the rearward (or leftward in FIG. 1) portion includes a plurality of evenly spaced tangs 16. In the depicted embodiment, four such tangs are included, positioned at 90-degree intervals around the nozzle, two of which are shown in phantom in FIG. 1. Alternatively, three or even two such tangs may be utilized.

With the cartridge 12 disposed in its partially inserted position depicted in phantom in FIG. 1, tangs 16 are displaced radially outwardly and are held there by cartridge walls 18. It is easy to insert cartridge 12 into this partially installed position because the walls 18 of the cartridge taper at 20 at the forward end thereof Tapered walls 20 thereby define an inner throat 21 disposed in the forward end of cartridge 12. An O-ring 22 is typically disposed adjacent this forward, tapered end of cartridge 12 between the cartridge and nozzle 14. A step 28 is included in the inner surface of side walls 30 of nozzle 14 to provide a stop and a sealing surface for O-ring 22 disposed between the tapered portion 20 of cartridge walls 18 and the inner surface of nozzle side walls 30. The O-ring thus prevents the flow of injectate along the interface between the outer surface of cartridge walls 18 and the inner surface of nozzle side walls 30. A plunger 24 is disposed within walls 18 of cartridge 12, and controls the injection of injectate out of the cartridge, as desired by the operator. At the factory, or at the user's location, cartridge 12 is inserted into nozzle 14, as shown in FIG. 1, and is then pressed forwardly and entirely into the nozzle, as shown in solid lines in FIG. 1, until the tapered portion 20 of walls 18 of cartridge 12 abut a cartridge abutment face 26 in the forward end of nozzle 14.

One advantage of the present invention is that it permits cartridge 12 to be prefilled with injectate and then stored at a suitable location, whether that be at the factory, at a hospital or other medical facility, a pharmacy, in an ambulance, or at the residence of a patient who may need the medication. Alternatively, cartridge 12 may be prefilled and stored in position within nozzle 14, ready to be inserted into a needleless injector, such as that shown generally at 32 in FIG. 3.

The needleless injector 32 with which the cartridge/nozzle assembly 10 is typically used is depicted in Peterson et al. U.S. Pat. No. 5,399,163, although the assembly 10 may be used in a wide variety of other needleless injection systems. The Peterson '163 patent is incorporated herein by reference. As shown in FIG. 3, the cartridge/nozzle assembly 10 is mounted to the front end 34 of injector 32 by a series of evenly spaced lugs 36, three of which are typically disposed at 120-degree intervals around the periphery of nozzle 14. The lugs 36 in nozzle 14 are aligned to pass through corresponding spaces 38 disposed in the front end 34 of injector 32. The cartridge/nozzle assembly 10 is then rotated to lock it in position such that lugs 36 are disposed between the inner surface 40 of front end 34 of injector 32 and a lug abutment surface 42 in injector 32. As the cartridge nozzle assembly 10 is inserted into injector 32, the forward end of a ram 44 abuts a somewhat resilient Teflon pad 45 mounted to the rearward end of the plunger 24. Contact between ram 44, pad 45 and plunger 24 is made prior to lugs 36 reaching lug abutment surface 42 in injector 32. As cartridge 12 is continued to be pushed into injector 32, with lugs 36 disposed against lug abutment surface 42, the ram 44, which is stationary, will cause plunger 24 to slide forward, which in consequence, will cause liquid injectate inside cartridge 12 to move outlet valve 46 forward, allowing flow of liquid into a recessed portion 50 and toward the jet orifice 52 (see FIG. 1). The amount of liquid flowing through outlet valve 46 during the insertion of cartridge 12 in injector 32 is controlled by the length of ram 44 relative to the inner surface 40.

Figure 4:
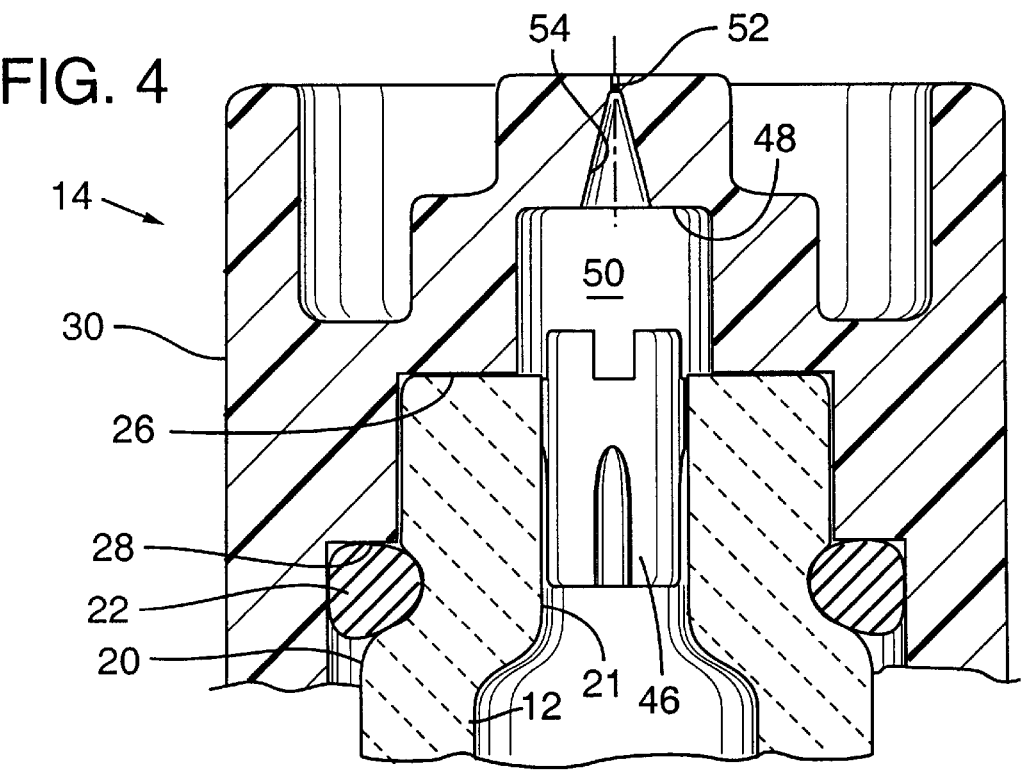
FIG. 4 is an enlarged, fragmentary, side elevation sectional view of the outlet valve and adjacent portions of the cartridge/nozzle assembly of the embodiment of FIG. 1, with the outlet valve shown in its unpressurized position.

As shown best in FIG. 4, an outlet valve 46 is disposed adjacent the inner surface of tapered walls 21 in the forward end of cartridge 12. This valve 46 is typically fabricated of butyl rubber or another resilient material which is a suitable drug storage material and is capable of being sterilized prior to insertion into cartridge 12. As shown in FIG. 4, valve 46 is designed to fit tightly within the forward end of cartridge 12. As best shown in FIGS. 6–10, the mid-portion or body 58 of outlet valve 46 is normally round in cross-section, and is sized such that it fits snugly within the tapered walls 20 of cartridge 12. The rearward portion of outlet valve 46 includes a plurality of (here four) slots 56 which extend rearwardly from a centrally disposed body portion 58 of outlet valve 46. The forward end 51 of outlet valve 46 includes forwardly extending members 62 which extend axially from body 58 of outlet valve 46 to define two perpendicular valve channels 64.

In the preferred embodiment, the outer diameter of the outlet valve is slightly greater than the inner diameter of tapered walls 21, with the outlet valve outer diameter being typically 0.105 inch, and the inner diameter of the taper walls being 0.098 inch. This difference in sizing, along with the somewhat elastic properties of butyl rubber or other material from which outlet valve 46 is formed, permits a friction fit in the front end of cartridge 12. However, once hydraulic pressure is exerted on outlet valve 46, such as when the cartridge/nozzle assembly 10 is pushed into place in needleless injector 32 while ram 44 is held stationary within the injector, outlet valve 46 is forced to a forward, initially-pressurized position depicted in FIG. 5, with the forward end of outlet valve 46 disposed against valve abutment surface 48 at the forward end of recessed portion 50 of the forward end of nozzle 14. This abutment surface 48 typically includes a surface or shoulder extending in a direction perpendicular to the longitudinal dimension of nozzle 14 and to the direction of displacement of outlet valve 46. The forward end 51 of outlet valve 46 typically includes a surface which complements that of the abutment surface shoulder, also extending perpendicular to the longitudinal dimension of the valve and to the direction of displacement of the valve. The forward end of recessed portion 50 terminates in a jet orifice 52 having a generally conical-shaped nozzle orifice channel 54. The relative sizing of the respective outlet valve 46, the inner surface of tapered walls 20, and recessed portion 50 are such that fluid is permitted to flow from the cartridge and into the recessed portion surrounding the outlet valve and perhaps even out of injection aperture 52.

Operation of the Embodiment of FIGS. 1–10

In operation, at the factory or at the user's location, cartridge 12 is inserted into nozzle 14 as shown in phantom in FIG. 1, and is then pressed forwardly and entirely into the nozzle, as shown in solid lines in FIG. 1 until the tapered portion 20 of walls 18 of cartridge 12 abut cartridge abutment face 26 in the forward end of nozzle 14. Prior to the mounting of the cartridge/nozzle assembly 10 within injector 32, as shown in FIGS. 1 and 4, outlet valve 46 is lodged in the throat 21 of cartridge 12 in its pre-initial pressure position. With the valve in this position, fluid disposed within the cartridge is prevented from flowing out of the throat 21 by the body portion 58 of valve 46.

Figure 5:
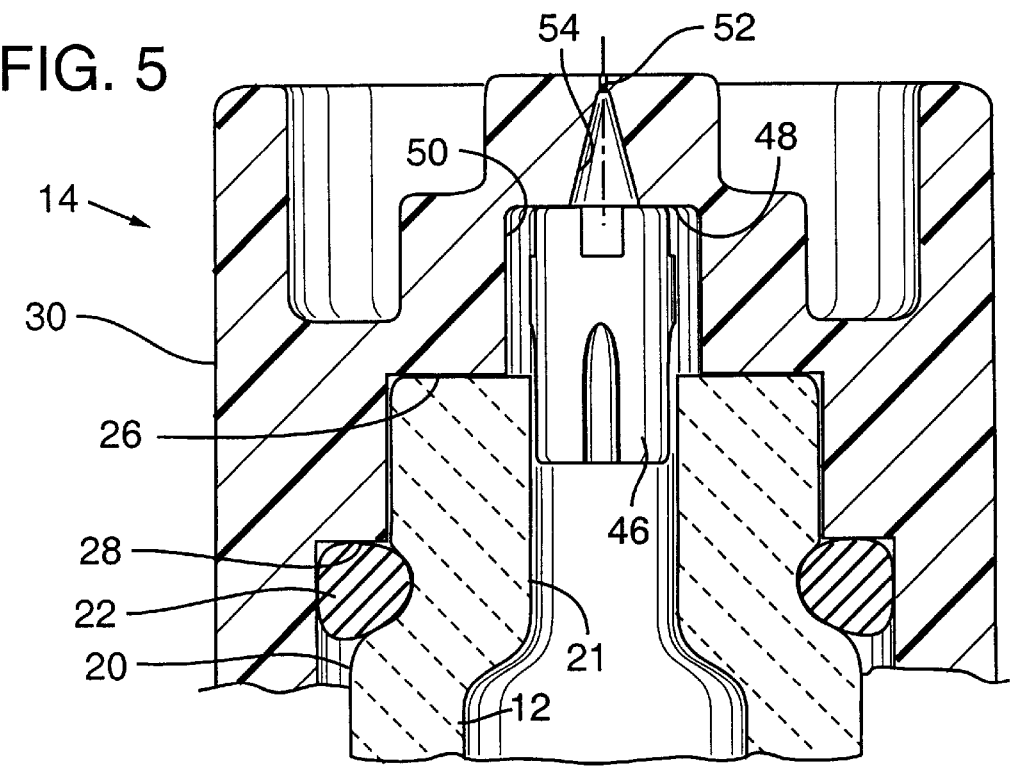
FIG. 5 is a view corresponding to FIG. 4 except that the outlet valve is shown in section and is shifted to its forward position.

Because ram 44 in injector 32 is held stationary, as the cartridge/nozzle assembly 10 is inserted into an injector 32, the pressure of plunger 24 against the fluid disposed in cartridge 12 causes outlet valve 46 to shift into its forward initially-pressurized position shown in FIG. 5. Because outlet valve 46 includes slots 56, fluid within the cartridge is permitted to flow through cartridge throat 21 and into cartridge recessed portion 50. Forward valve channels 64 in outlet valve 46 permit the fluid rushing into recessed portion 50 to displace any air in the recessed portion, forcing that air out orifice channel 54 and orifice 52, so that the recessed portion, the orifice channel, and the aperture are all entirely filled with injectate. This may also result in some injectate dribbling out the jet orifice, but because it is an insignificant amount, it is of little concern. What is important is that all of the air is displaced from the front of nozzle 14. This permits the amount of injectate which will be injected into the patient to be precisely measured, which would not be possible if an unknown amount of air was disposed in the front of the nozzle. This also permits pressure to be precisely predetermined, again, which would not be possible if an undetermined amount of air was disposed in the front of the nozzle.

This step of insertion of the cartridge/nozzle assembly 10 into injector 32 is typically performed immediately prior to injection. Thus, with assembly 10 in place, the needleless injector 32 can be activated, forcing ram 44 and plunger 24 forwardly, thereby driving injectate through slots 56 in outlet valve 46, around body 58 disposed within recessed portion 50, through valve channels 64 and into aperture channel 54 and aperture 52 and into the patient. Because of the configuration of outlet valve 46, throat 21 and the inner walls of recessed portion 50, there is very little pressure drop as fluid is being forced out of the cartridge and out of injection aperture 52.

Figure 11:
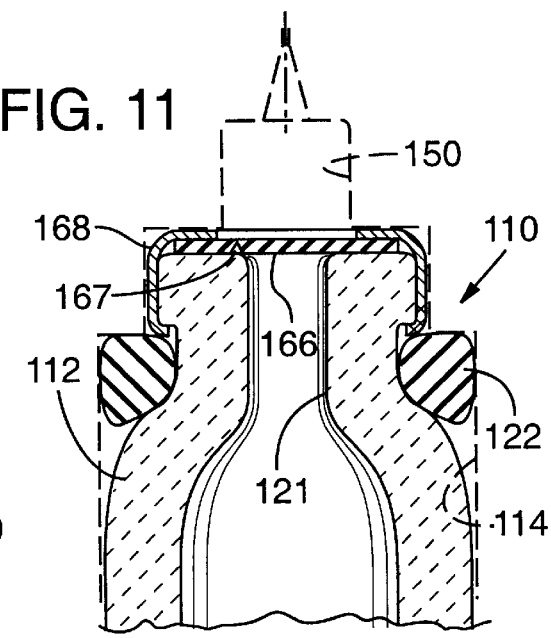
FIG. 11 is a side elevation sectional view of an alternate embodiment showing a membrane in place of the outlet valve.
Figure 12A:
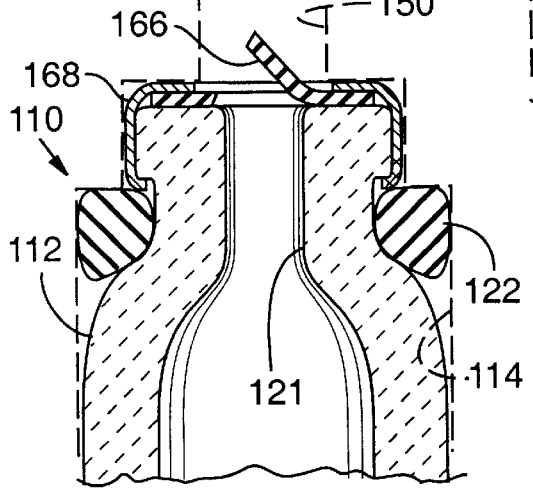
FIG. 12A is a side elevation view of the embodiment of FIG. 11, with the membrane broken.
Figure 12B:
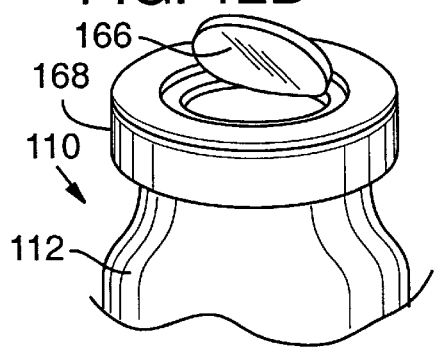
FIG. 12B is an isometric view corresponding to FIG. 12A.

The Embodiment of FIGS. 11, 12A and 12B

FIGS. 11, 12A and 12B depict an alternate embodiment of the prefilled cartridge/nozzle assembly, indicated generally at 110. In place of an outlet valve, embodiment 110 includes an elastomeric membrane 166 which is designed to burst open when a predetermined pressure has been applied, as shown in FIGS. 12A and 12B. Membrane 166 normally has a weakened portion along which the break will occur. In the depicted embodiment this weakened portion takes the form of a notch 167 which extends most but not all of the 360° around the inner throat 121 of cartridge 112. Membrane 166 is typically held in place by an aluminum seal 168 which is often used to help seal medication-containing cartridges.

In other respects embodiment 110 is much like embodiment 10 in that it includes O-rings 122 and nozzle 114, and is typically prefilled with injectate. Membrane 166 is designed to burst open when it is loaded into a needleless injector system as the plunger (not shown) is slightly depressed by the injector ram (not shown) as explained earlier. Upon bursting of membrane 166, injectate flows into the recess 155 in the forward end of the nozzle 114, thereby displacing any air and preparing the assembly for an injection.

Figure 13A:
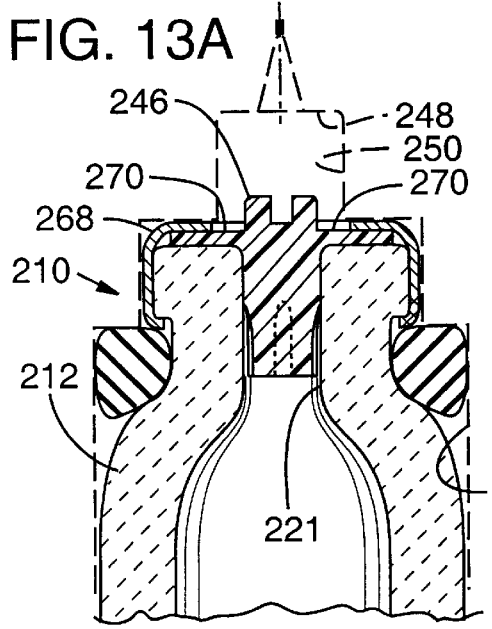
FIG. 13A is a side elevation sectional view of a second alternate embodiment, with the outlet valve in its closed position.
Figure 13B:
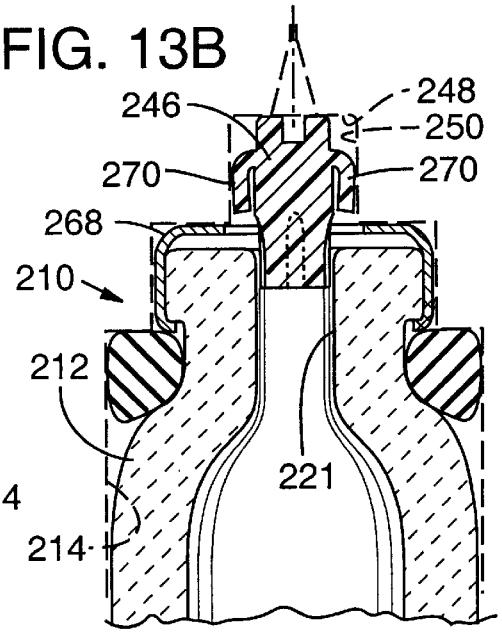
FIG. 13B is a view corresponding to FIG. 13A except that the outlet valve is shown in its forward position.

The Embodiment of FIGS. 13A and 13B

FIGS. 13A and 13B depict another alternate embodiment of the cartridge/nozzle assembly, indicated generally at 210. This embodiment utilizes an aluminum seal 268 like embodiment 110, but also includes an outlet valve 246. Outlet valve 246 includes a pair of radially extending wings 270 which are clamped under aluminum seal 268 until a predetermined amount of pressure forces outlet valve 246 out of the inner throat 221 of cartridge 212. When this predetermined pressure is reached, wings 270 pull out from seal 268 and the valve shifts forwardly into the nozzle recessed portion 250 of nozzle 214 until it comes into contact with the nozzle abutment surface 248.

Other than the presence of wings 270, outlet valve 246 is the same as the previously described outlet valve 46 in the cartridge/nozzle assembly 10 of FIGS. 1–10. Thus, when outlet valve 246 is shifted to its forward position depicted in FIG. 13B, injectate is permitted to flow out of cartridge 212 and into recessed portion 250 to displace any air and thus prepare the assembly 210 for an injection, as described above.

Figure 14A:
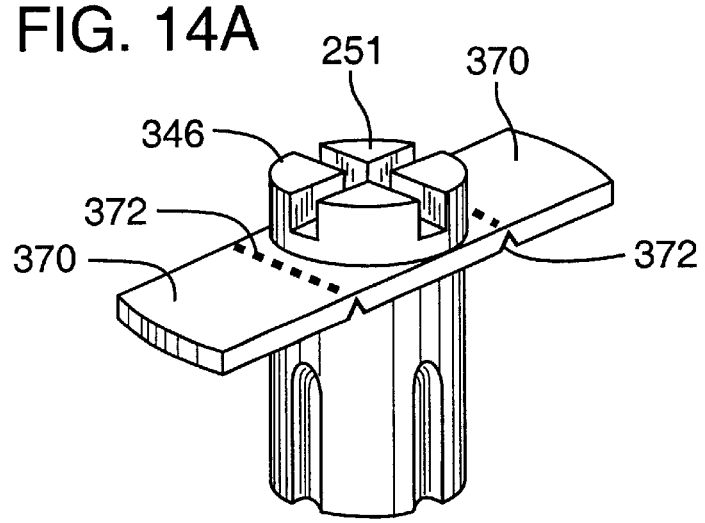
FIG. 14A is an isometric view of an outlet valve corresponding to the outlet valve depicted in FIGS. 13A and B except that the valve wings are notched to facilitate tearing when pressure is exerted on the valve.
Figure 14B:
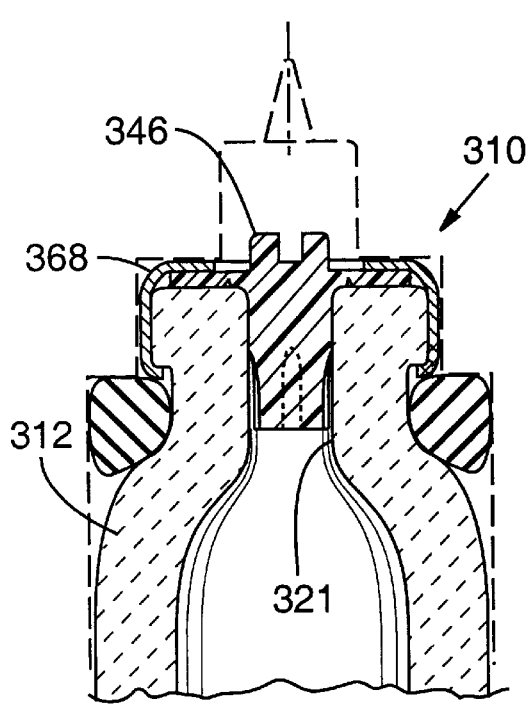
FIG. 14B is a view corresponding to FIG. 13A except that the notched-wing version of the outlet valve, shown in FIG. 14A, is depicted.
Figure 14C:
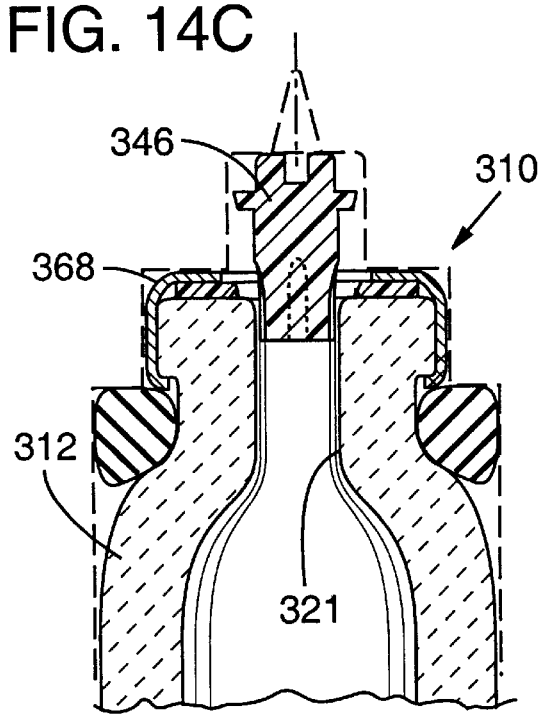
FIG. 14C corresponds to FIG. 14B except that the outlet valve is shown in its open position.

The Embodiment of FIGS. 14A–C

The cartridge/nozzle assembly 310 of FIGS. 14A–C is identical to assembly 210 except that wings 370 of outlet valve 346 include weakened portions. In the depicted embodiment these weakened portions take the form of a pair of notches 372. Thus, when the cartridge/nozzle assembly 310 is mounted into a needleless injection system (not shown), instead of wings 370 pulling out of engagement with seal 368, the wings typically tear at notches 372 to permit outlet valve 346 to shift to the forward position depicted in FIG. 14C. In other respects the operation of cartridge/nozzle assembly 310 is the same as assemblies 10 and 210 described above.

Figure 15:
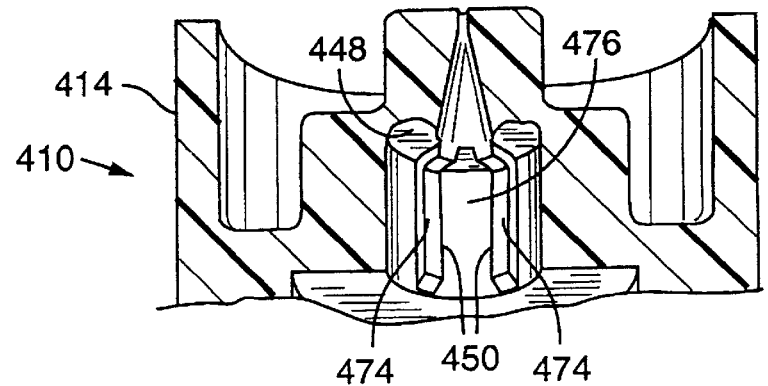
FIG. 15 is a fragmentary side elevation sectional view of yet another alternate embodiment of the nozzle without the cartridge or the outlet valve, showing ribs in the nozzle recess.
Figure 16A:
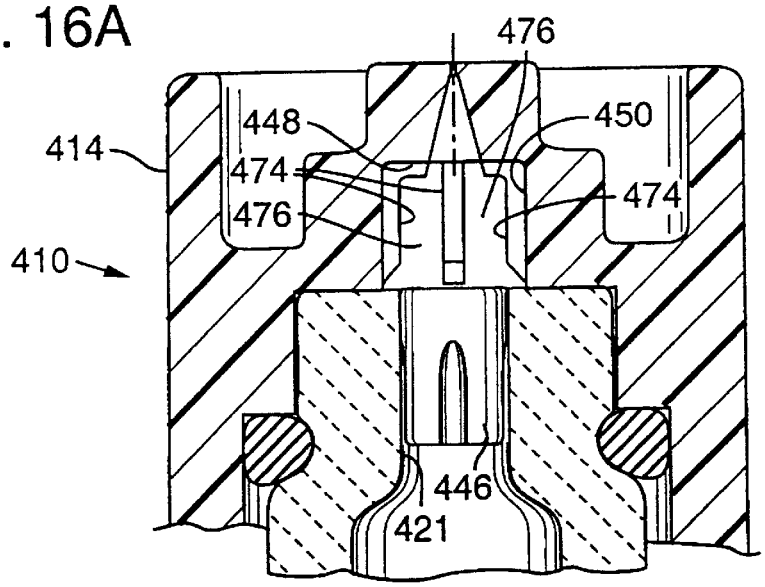
FIG. 16A is an enlarged side elevation sectional view of the embodiment of FIG. 15, showing the cartridge and the outlet valve in its closed position.
Figure 16B:
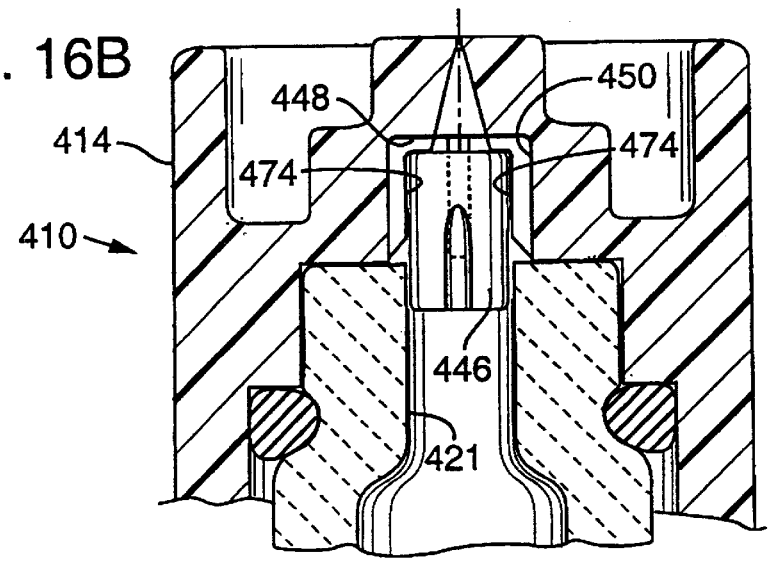
FIG. 16B is a view corresponding to FIG. 1 6A except that the outlet valve is shown in its forward position.

The Embodiment of FIGS. 15, 16A and 16B

The cartridge/nozzle assembly 410 of FIGS. 15, 16A and 16B is identical to assembly 10 in FIGS. 1–10 except that recessed portion 450 of nozzle 414 includes a plurality of evenly spaced ribs 474. In the depicted embodiment four such ribs 474 are included. They first extend along the walls of recessed portion 450 in a direction parallel to the path of travel of outlet valve 446, and then extend radially along abutment surface 448. The portions extending along the walls of recessed portion 450 are sized such that outlet valve 446 fits snugly into the recessed portion, as shown in FIG. 16B, with the inner diameter of the space defined between ribs 474 being slightly less than the inner diameter of cartridge throat 421. This slight difference in the inner diameters prevents outlet valve 446 from inadvertently shifting forward during thermal changes and the minor pressure changes resulting therefrom. The relative sizing of these inner diameters permits the opening pressure of the outlet valve to be controlled.

Channels 476 are thus defined between ribs 474 permit fluid to flow around outlet valve 446 to orifice 52. Because fluid flow is facilitated so well, this is actually the most preferred embodiment of the invention. In other respects cartridge/nozzle assembly 410 is constructed and operates in the same manner as assembly 10 of FIGS. 1–10.

The Embodiment of FIGS. 17A and B

FIGS. 17A and B depict another alternate embodiment of the cartridge/nozzle assembly shown generally at 510. The assembly includes a cartridge 512 and a nozzle 514. Cartridge 512 is prefilled with injectate as described above and is sealed with an aluminum seal 568 and an elastomeric membrane 566, normally fabricated of butyl rubber. A spike 578 is provided to pierce membrane 566 when the cartridge is inserted all of the way into position in the nozzle, as shown in FIG. 17B. The spike includes an internal channel 580 which is in fluid contact with orifice 552. An O-ring seal 522 is provided to prevent leakage between the cartridge and the nozzle.

Thus, in use, cartridge 512 is placed within nozzle 514 to a position such that spike 578 approaches but does not pierce membrane 566. Then, immediately prior to injection cartridge 512 is pushed all the way into nozzle 514, causing spike 578 to pierce membrane 566 so that injectate is permitted to flow through spike channel 580 to orifice 552 to displace any air in the channel. The orifice is then placed against the skin of the patient and the injector (not shown) is activated, causing injectate to be forced out of cartridge 512, into spike 578, through spike channel 580 and orifice 552 and into the patient.

In other respects, cartridge/nozzle assembly 510 is the same in structure and operation as the previously described embodiments.

Other changes and modifications of the present invention can be made without departing from the spirit and scope of the present invention. Such changes and modifications are intended to be covered by the following claims.

I claim:

1. A cartridge and nozzle assembly for use in a needleless injection system, comprising:
   a cartridge having a plunger disposed at a rearward end thereof, and including a throat at a forward portion thereof, the cartridge further including a generally laterally extending interface surface;
   a displaceable outlet valve initially disposed within the cartridge throat, the outlet valve being formed of resilient material;
   a nozzle for receiving the cartridge, the nozzle defining a rearward, cartridge-receiving portion, and including a forward portion terminating in and defining a valve abutment surface with an injection orifice defined therein, the forward portion being configured to receive the valve when the valve is displaced to a forwardly disposed position such that the valve is disposed against the valve abutment surface, with a plurality of channels providing fluid access between the cartridge throat and the injection orifice when the valve is in its forwardly disposed position, the nozzle further including a generally laterally extending interface surface which abuts the cartridge interface surface; and
   a seal disposed between the cartridge and the nozzle rearward of the interface surfaces for at least reducing leakage of injectate therebetween.

2. The assembly of claim 1, wherein the cartridge includes a peripheral seal positioned over at least a portion of the outlet valve for retaining the outlet valve in place to keep the cartridge closed and sealed until the cartridge is sufficiently pressurized.

3. The assembly of claim 2 wherein the outlet valve includes a radially extending portion adjacent the forward portion thereof, at least a part of the radially extending portion being covered by the peripheral seal when the outlet valve is in its closed position.

4. The assembly of claim 3 wherein the radially extending portion includes a weakened region disposed radially inwardly of the peripheral seal which is subject to tearing to permit the outlet valve to shift forwardly to open the cartridge.

5. The assembly of claim 1 wherein the cartridge throat is tapered and the seal is mounted in a gap defined between the cartridge and the nozzle, adjacent to the cartridge throat.

6. The assembly of claim 1 wherein the valve abutment surface includes a shoulder extending perpendicular to the path of travel of the valve, and the valve includes a complementary surface which also extends perpendicular to the path of travel of the valve.

7. The assembly of claim 1 wherein the rearward portion of the outlet valve extends at least partially into the cartridge throat when the forward portion thereof is disposed against the abutment surface.

8. The assembly of claim 1 wherein the cartridge is formed of glass.

9. The assembly of claim 1 wherein the valve is sized to be friction fit within the cartridge throat, and the valve includes a channel-less valve body adopted to be fit against the cartridge throat when the valve is in its initial position.

10. The assembly of claim 9 wherein the seal is disposed rearwardly of the initial position of the valve body.

11. The assembly of claim 1 wherein the cartridge throat includes a rearward end, and the seal is disposed in alignment with the rearward end of the cartridge throat.

12. The assembly of claim 1 wherein the outlet valve has a channel-less valve body so that the throat is sealed when the valve is disposed within the throat.

13. The assembly of claim 1 wherein the plurality of channels are formed in the outlet valve.

14. The assembly of claim 1 wherein the cartridge interface surface is generally forwardly facing, and the nozzle interface surface is generally rearwardly facing.

15. A method of providing a needleless injection system, comprising:

selecting a resilient valve member;

selecting a cartridge having laterally facing side walls, a forward throat conforming to the body of the valve;

placing the valve within the cartridge throat;

filling the cartridge with liquid injectate;

installing a plunger in the rear end of the cartridge;

selecting a nozzle with laterally facing side walls, a rearward cartridge-receiving portion and a forward portion defining a recess for non-sealably receiving the valve such that a plurality of channels are defined between the valve and the nozzle, the nozzle further including an orifice for facilitating injection of injectate therethrough;

selecting a cartridge/nozzle seal member;

installing the cartridge into the nozzle to form a cartridge/nozzle assembly, with the seal member disposed between the side walls of the cartridge and nozzle; and mounting the cartridge/nozzle assembly into a needleless injection system by pushing the plunger rearwardly against a ram to forwardly displace the plunger, causing pressure of injectate within the cartridge to forwardly displace the valve into the nozzle recess to permit injectate to flow through the channels, and into the orifice.

16. The method of claim 15, further comprising:

subsequently having the ram exert injection pressure on the plunger to force injectate from the cartridge, through the channels and through the aperture and into the patient.

17. The method of claim 15 wherein the step of selecting the valve involves selecting a valve having a radially-outwardly extending surface with a tearable portion defined therein, and wherein the step of pushing the plunger and causing pressure to forwardly displace the valve involves tearing the tearable portion and thereby permitting the valve to be forwardly displaced.

* * * * *

UNITED STATES PATENT AND TRADEMARK OFFICE
CERTIFICATE OF CORRECTION

PATENT NO.   : 6,132,395
DATED        : October 17, 2000
INVENTOR(S)  : Landau et al.

It is certified that error appears in the above-identified patent and that said Letters Patent is hereby corrected as shown below:

Title page,
Item [57] ABSTRACT,
Line 1, please replace the word "needless" with -- needleless --.

Column 1,
Line 66, please replace the word "needless" with -- needleless --.

Signed and Sealed this

Fifth Day of March, 2002

Attest:

JAMES E. ROGAN
*Attesting Officer*       *Director of the United States Patent and Trademark Office*